United States Patent [19]

Thieme et al.

[11] Patent Number: 4,748,250
[45] Date of Patent: May 31, 1988

[54] DIASTEREOSELECTIVE REDUCTION OF ALPHA-TRIAZOLYLKETONES TO BETATRIAZOLYLCARBINOLS

[75] Inventors: Peter C. Thieme, Wachenheim; Hubert Sauter, Mannheim; Gernot Reissenweber, Boehl-Iggelheim, all of Fed. Rep. of Germany

[73] Assignee: BASF Aktiengesellschaft, Ludwigshafen, Fed. Rep. of Germany

[21] Appl. No.: 729,951

[22] Filed: May 2, 1985

[30] Foreign Application Priority Data

May 4, 1984 [DE] Fed. Rep. of Germany ....... 3416444
Nov. 23, 1984 [DE] Fed. Rep. of Germany ....... 3442657

[51] Int. Cl.$^4$ .......................................... C07D 249/08
[52] U.S. Cl. .................................................... 548/262
[58] Field of Search ............... 548/262, 341; 568/846, 568/874, 876

[56] References Cited

U.S. PATENT DOCUMENTS

| | | | |
|---|---|---|---|
| 3,952,002 | 4/1976 | Kramer et al. | 548/262 |
| 3,972,892 | 3/1976 | Büchel et al. | 548/262 |
| 4,232,033 | 11/1980 | Krämer et al. | 548/262 |
| 4,243,405 | 1/1981 | Balasubramanyan et al. | 71/76 |
| 4,380,546 | 4/1983 | Sauter et al. | 548/262 |

FOREIGN PATENT DOCUMENTS

| | | | |
|---|---|---|---|
| 3321023 | 12/1984 | Fed. Rep. of Germany | 548/262 |
| 0186964 | 10/1984 | Japan | 548/262 |
| 2041927 | 9/1980 | United Kingdom | 548/262 |

OTHER PUBLICATIONS

Roher et al, "Tetrabutylammonium horobydride, etc" JOC, 41 (1976) 690.
Hirao et al "Asymmetric reduction, etc" CA 92:128500e (1980).

Primary Examiner—Glennon H. Hollrah
Assistant Examiner—Patricia L. Morris
Attorney, Agent, or Firm—Keil & Weinkauf

[57] ABSTRACT

Sterically pure β-triazolyl carbinols of the general structure

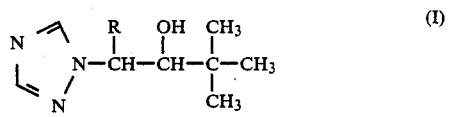

where R is not hydrogen, in particular the R*, S*-diastereomer, are obtained by diastereoselective reduction of the corresponding α-triazolylketone with a complex hydride which reduces ketones to alcohols, in the presence of a Lewis acid in a non-polar solvent.

4 Claims, No Drawings

DIASTEREOSELECTIVE REDUCTION OF ALPHA-TRIAZOLYLKETONES TO BETATRIAZOLYLCARBINOLS

The present invention relates to a process for the diastereoselective reduction of α-triazolylketones to β-triazolylcarbinols.

It is known that the diastereomers of triazolyl alcohols have a more or less powerful action against certain phytopathogenic fungi. For example, the only diastereomer which possesses high activity is the one whose two enantiomers have the steric arrangement Ia.

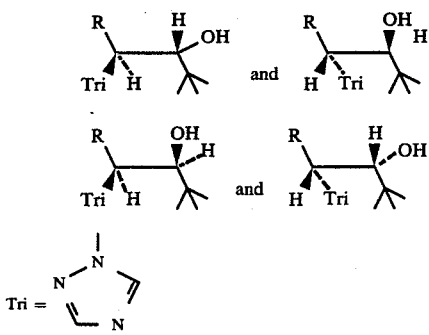

Where R is 4-chlorophenoxy, the enantiomer mixture Ia corresponds to the R*, S*-triadimenol diastereomer, which has the greater fungicidal activity (W. Krämer, K.H. Büchel and W. Draber, 5th International Congress of Pesticide Chemistry IUPAC Kyoto 1982 (Abstr. II s-3)). By way of explanation, it is noted that compounds possessing two different chiral carbon atoms form four stereoisomers whose configuration can be named according to the Cahn-Ingold-Prelog system (cf. for example D. Seebach and V. Prelog, Angew. Chem. 94 (1982), 696 and the literature cited therein). Two enantiomers having the configurations R, R and S, S constitute a diastereomer denoted by R*, R*. The other diastereomer, which is named R*, S*, is composed of the two enantiomers having the configurations R, S and S, R.

German Laid-Open Application DOS No. 3,019,049 describes examples of compounds of the above formula I (for example, where R is 4-phenoxybutyl) which must consist of the diastereomer mixtures R*, R* and R*, S*, the R*, R* diastereomers predominating because the preparation is carried out using the corresponding ketones, with the aid of sodium boranate (sodium borohydride). The fungicidal action of the diastereomers of the configuration R*, R* is substantially smaller than that of the diastereomers with the configuration R*, S*.

It is an object of the present invention to provide a process which permits the selective preparation of the more effective diastereomer.

We have found that this object is achieved, and that the reaction of the corresponding ketones with a complex hydride which reduces the ketone to an alcohol predominantly gives the desired R*, S* isomer, if the reaction is carried out in a solvent, which is preferably non-polar, in the presence of a Lewis acid, such as a zinc halide or titanium halide (e.g. titanium tetrachloride or an alkoxy-titanium chloride).

The present invention therefore relates to a process for the diastereoselective preparation of β-triazolylcarbinols

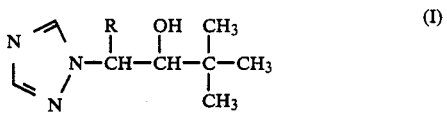

where R is
(a) phenoxy which is unsubstituted or substituted by halogen, CF$_3$, alkyl, alkoxy, phenyl or phenoxy, or
(B) C$_1$–C$_{10}$-alkyl which is unsubstituted or monosubstituted or polysubstituted by identical or different radicals from the group consisting of alkoxy, alkyl, aryl and aryloxy, which in turn can be substituted by halogen, CF$_3$, alkyl or alkoxy,
by diastereoselective reduction of the corresponding α-triazolylketone with a complex metal hydride which reduces ketones to alcohols, in the presence of a Lewis acid, wherein the reaction is carried out in an aprotic, preferably non-polar solvent.

Examples of Lewis acids which are used are zinc chloride, tin tetrachloride, titanium tetrachloride, zinc bromide, magnesium chloride, boron trifluoride, titanium tetrabromide and alkoxy-titanium chlorides of the general formula (R'O)$_o$TiCl$_p$ where o and p are, respectively, 1 and 3, 2 and 2, or 3 and 1, and R' is lower alkyl, preferably isopropyl. The Lewis acids are preferably employed in the same molar amount as the ketone.

The reducing agent is advantageously used in the form of a salt which is soluble in non-polar solvents, e.g. as tetra-n-butylammonium boranate. Other boranates, such as tetramethylammonium, tetraethylammonium, trimethylbenzoylammonium boranate and the corresponding aluminum compounds, can also be used. If lithium boranate, sodium boranate or potassium boranate is used, the poor solubility of these boranates in non-polar solvents makes it necessary to use suitable assistants to ensure that the boranate passes into the organic phase. Where lithium borohydride is used, admixing ethers, such as diethyl ether, methyl t-butyl ether or tetrahydrofuran, may improve the solubility.

Preferred solvents are halohydrocarbons, e.g. chloroform, methylene chloride or dichloroethane, toluene and mixtures of these.

The substituent R is, for example,
phenoxy,
4-chlorophenoxy,
2,4-dichlorophenoxy,
4-bromophenoxy,
2-chlorophenoxy,
2-fluorophenoxy,
4-fluorophenoxy,
3-trifluoromethylphenoxy,
2,4-dimethylphenoxy,
2,4,6-trichlorophenoxy,
4-methylphenoxy,
2-methoxyphenoxy,
4-phenylphenoxy,
3-phenylphenoxy,
3-phenoxyphenoxy,
4-phenoxyphenoxy,
benzyl,
4-chlorobenzyl,
2,4-dichlorobenzyl,
2-fluorobenzyl,
4-fluorobenzyl,
2-chlorobenzyl,
2-bromobenzyl, 2,4-dimethylbenzyl,
4-methoxybenzyl,
2-methyl-3-phenylprop-1-yl,
3-phenylpropyl,
4-phenylbutyl,
4-phenoxybenzyl,
2-phenylethyl,
2-phenoxyethyl,
3-phenoxypropyl,
4-phenoxybutyl,
2-(2-fluorophenoxy)-ethyl,
4-(2-fluorophenoxy)-butyl,
2-(4-tert.-butylphenoxy)-ethyl,
2,2,2-trimethylethyl,
n-decyl,
n-octyl,
2-ethoxyethyl,
4-(3-trifluoromethylphenoxy)-butyl or
4-(3-chlorophenoxy)-butyl.

In the process according to the invention, the ketone is dissolved in about 8–15 parts by weight of the solvent, and the appropriate amount (e.g. from 0.3 to 1.2, preferably about 0.95–1.05, mol equivalents) of, for example, titanium tetrachloride, zinc chloride or another Lewis acid from amongst those stated above is added to the cooled solution. Thereafter, a solution or suspension of the complex hydride in the appropriate solvent is added dropwise at from −30° C. to room temperature, preferably about 0° C., or the hydride is added in solid form. For example, the hydride is used in an excess of from 0.1 to 2 mol equivalents. Suitable complex hydrides are all complex metal hydrides which reduce carbonyl functions to alcohols, e.g. Na8H$_4$, LiBH$_4$, R$^4$NBH$_4$, where R is H, C$_1$–C$_6$-alkyl or aralkyl, LiAlH$_4$ or diisobutylaluminum hydride (Dibal-4). If lithium alanate is used, it may also be added in the form of tablets.

The mixture is allowed to reach room temperature, and stirring is continued until monitoring by thin layer chromatography shows that the ketone has been consumed. This takes up to 60 hours, depending on the reducing agent used. The mixture is then again cooled to 0° C., water and dilute hydrochloric acid or an aqueous base, e.g. sodium hydroxide, are added, and working up is carried out in a conventional manner. The crude product, which is obtained in yields of, in general, from greater than 50% to greater than 90%, predominantly or exclusively contains the diastereomer having the configuration R*, S*. The configuration can be determined by analyzing the NMR spectrum.

Thus, a process is available which virtually exclusively gives the desired diastereomer R*, S* in very good yield, under mild conditions. Compared with the process described in German Laid-Open Application DOS No. 3,019,049, the novel process has the advantage that it is possible to dispense with separation of the diastereomers for obtaining the R*,S* diastereomer, such a separation entailing considerable loss of substance.

EXAMPLE 1

5.69 g (0.03 mole) of titanium tetrachloride in 20 ml of methylene chloride are added to 7.87 g (0.025 mole) of 8-phenoxy-4-(1,2,4-triazol-1-yl)-2,2-dimethyloctan-3-one in 130 ml of methylene chloride at −30° C. The mixture is stirred at room temperature for 30 minutes and then cooled again to −30° C., and 3.2 g (0.0125 mole) of tetra-n-butylammonium borohydride in 20 ml of methylene chloride are added dropwise. Stirring is continued for one hour at room temperature, after which 200 ml of distilled water are added slowly, the mixture is substantially acidified with 10% strength acid, and the methylene chloride phase is separated off. Extraction by shaking with methylene chloride is carried out once again, and the organic phase is washed with dilute hydrochloric acid, bicarbonate solution and water, dried and evaporated down.

6.48 g (82% of theory) of solid crude product are obtained, this product virtually exclusively containing the desired R*, S* diastereomer (9H singlets at 1.0 ppm). After recrystallization once from toluene, the product has a melting point of 132°–133° C.

COMPARISON

The experiment of Example 1 is carried out without the addition of TiCl$_4$, and 6.2 g (78% of theory) of crude product are obtained. According to the NMR spectrum, this product contains the two diastereomeric carbinols R*, S* and R*, R* in a ratio of 1:9 (9H singlets at 1.0 and 0.7 ppm); this corresponds to 8% of the desired product R*, S*.

EXAMPLE 2

6.43 g (0.025 mole) of 5-phenyl-4-(1,2,4-triazol-1-yl)-2,2-dimethylpentan-3-one are converted as described in Example 1 to give 6.17 g (95% of theory) of crude product which contains the two diastereomeric carbinols R*, S* and R*, R* in a ratio of 95:5 (9H singlets at 1.0 and 0.7 ppm in a ratio of 95:5).

EXAMPLE 3

8.3 g (0.025 mole) of 8-(o-fluorophenoxy)-4-(1,2,4-triazol-1-yl)-2,2-dimethyloctan-3-one are converted as described in Example 1 to give 8.1 g (97% of theory) of the diastereomeric carbinols R*, S* and R*, R* in a ratio of 95:5.

EXAMPLE 4

8.3 g (0.025 mole) of 8-(o-fluorophenoxy)-4-(1,2,4-triazol-1-yl)-2,2-dimethyloct-6-en-3-one are converted as described in Example 1 to give 8.2 g (99% of theory) of crude product which contains the diastereomeric carbinols R*, S* and R*, R*, once again in a ratio of 95:5.

EXAMPLE 5

7.3 g (0.025 mole) of 1-(p-chlorophenoxy)-1-(1,2,4-triazol-1-yl)-3,3-dimethylbutan-2-one are converted as described in Example 1 to give 7.2 g (98% of theory) of crude product which contains the two diastereomeric carbinols R*, R* and R*, S* in a ratio of 7:3 (9H singlets at 1.1 and 0.8 ppm in a ratio of 7:3).

EXAMPLE 6

8.2 g (0.025 mole) of 1-(2,4-dichlorophenoxy)-1-(1,2,4-triazol-1-yl)-3,3-dimethylbutan-2-one are converted as described in Example 1 to give 8.1 g (98% of theory) of crude product which contains the two diastereomeric carbinols R*, R* and R*, S* in a ratio of 4:1 (9H singlets at 1.0 and 0.8 ppm in a ratio of 4:1).

EXAMPLE 7

4.1 g (0.03 mole) of zinc chloride dried under greatly reduced pressure are dissolved in 4.5 g (0.06 mole) of anhydrous diethyl ether, and the solution is diluted with 100 ml of methylene chloride (clear solution). 7.8 g (0.025 mole) of 5-phenyl-4-(1,2,4-triazol-1-yl)-2,2- dimethylpentan-3-one in 40 ml of $CH_2Cl_2$ are added to this solution at $-30°$ C., the mixture is stirred for half an hour at room temperature and cooled to $-30°$ C., and 3.2 g (0.0125 mole) of tetrabutylammonium boranate in 20 ml of methylene chloride are added dropwise. Stirring is continued for a further 15 hours at room temperature, after which working up is carried out as described in Example 1 to give 4.7 g (59% of theory) of crude product which contains the two diastereomeric carbinols R*, S* and R*, R* in a ratio of 9:1 (9H singlets at 1.0 and 0.7 ppm in a ratio of 9:1).

EXAMPLE 8

11.38 g (0.06 mole) of titanium tetrachloride are added to a solution of 15.75 g (0.05 mole) of 8-phenoxy-4-(1,2,4-triazol-1-yl)-2,2-dimethyloctan-3-one in 150 ml of methylene chloride at $-50°$ C. in the course of 15 minutes, and stirring is continued for 30 minutes at this temperature. Thereafter, 50 ml of tetrahydrofuran are added, the mixture is warmed to 0° C., and 1 g (0.026 mole) of lithium aluminum chloride (tablet form) is added. The stirred mixture is allowed to reach room temperature slowly, and is stirred for a further 70 hours. It is then poured onto 200 ml of ice water and acidified with 10% strength aqueous hydrochloric acid. The methylene chloride phase is separated off, the aqueous phase is again extracted by shaking with methylene chloride, and the methylene chloride phase is washed neutral, dried and evaporated down to give 14.26 g (90% of theory) of solid crude product. The NMR spectrum (200 MHz) shows that this product is a mixture of

| Educt | <5% | (9 H singlets at 1.2 ppm) |
|---|---|---|
| R*, S*-carbinol | about 72% | (9 H singlets at 1.0 ppm) |
| R*, R*-carbinol | about 23% | (9 H singlets at 0.7 ppm). |

Recrystallization once from toluene gives 6.31 g (40% of theory) of pure R*, S*-carbinol of melting point 132°–133° C.

COMPARISON EXPERIMENT FOR EXAMPLE 7

The procedure described in Example 7 is followed, except that the addition of titanium tetrachloride is omitted, and 13.3 g (83% of theory) of solid crude product are obtained. The NMR spectrum (200 MHz) shows that this product is a mixture of

| Educt | <2% | |
|---|---|---|
| R*, S*-carbinol | 56% | (9 H singlets at 1.0 ppm) |
| R*, R*-carbinol | 44% | (9 H singlets at 0.7 ppm). |

EXAMPLE 8

2.85 g (0.015 mole) of titanium tetrachloride and 4.25 g (0.015 mole) of tetraisopropoxy titanate are added together to 130 ml of methylene chloride at $-30°$ C., and the mixture is warmed to room temperature and kept at this temperature for 0.5 hour. This procedure gives diisopropoxy-titanium dichloride. The mixture is cooled to $-30°$ C., after which 7.87 g (0.025 mole) of 8-phenoxy-4-(1,2,4-triazol-1-yl)-2,2-dimethyloctan-3-one in 40 ml of methylene chloride are added, stirring is continued for half an hour, and 3.2 g (0.0125 mole) of tetra-n-butylammonium borohydride in 20 ml of methylene chloride are then added dropwise at 0° C. The mixture is worked up to give 5.1 g (64% of theory) of crude product, which contains the diastereomeric carbinols R*, S* and R*, R* in a ratio of 9:1 (9H singlets at 1.0 and 0.7 ppm in a ratio of 9:1).

EXAMPLE 9

7.6 g (0.04 mole) of titanium tetrachloride in 20 ml of dichloromethane are added to 12.8 g (0.04 mole) of 8-phenoxy-4-(1,2,4-triazol-1-yl)-2,2-dimethyloct-6-en-3-one in 50 ml of dichloromethane at $-30°$ C., after which a suspension of 1.8 g (0.02 mole) of tetramethylammonium borohydride in 20 ml of dichloromethane is added a little at a time while cooling, the temperature increasing to $-5°$ C. The mixture is left for one hour at room temperature and then poured onto a cooled solution of 12.8 g of sodium hydroxide in 200 ml of water, insoluble material is filtered off, and the organic phase of the filtrate is separated off, washed twice with water, dried over magnesium sulfate and evaporated to dryness under reduced pressure. The crystalline residue (10.8 g, 84% of theory) contains virtually pure R*,S*-8-phenoxy-4-(1,2,4-triazol-1-yl)-2,2-dimethyloct-6-en-3-ol, the amount of R*,R*-diastereomer being less than 3% ($^1$H-NMR).

EXAMPLE 10

5.7 g (0.03 mole) of titanium tetrachloride in 20 ml of dichloromethane are added to 9.82 g (0.025 mole) of 6-(4-tert.-butylphenoxy)-4-(1,2,4-triazol-1-yl)-2,2-dimethylhexan-3-one in 50 ml of dichloromethane at $-30°$ C., the mixture is stirred for 0.5 hour, and 3.2 g (0.0125 mole) of tetrabutylammonium borohydride in 20 ml of dichloromethane are then added. The mixture warms up to room temperature, and is stirred at this temperature for a further 6 hours. 80 ml of 10% strength HCl are added and 7.1 g (71% of theory) of a solid of melting point 157°–160° C. are obtained.

$C_{20}H_{31}N_3O_2 \cdot HCl \cdot H_2O$ (398.5): calculated: C,60.07%; H,8.51%; N,10.50%. found: C,59.4%; H,8.6%; N,10.0%.

The $^1$H-NMR spectrum shows that the amount of R*,S*-6-(4-tert.-butylphenoxy)-4-(1,2,4-triazol-1-yl)-2,2-dimethylhexan-3-ol is more than 97%.

EXAMPLE 11

8.3 g (0.025 mole) of 8-(o-fluorophenoxy)-4-(1,2,4-triazol-1-yl)-2,2-dimethyloctan-3-one are converted by a procedure similar to that described in Example 1, except that 7.8 g (0.03 mole) of tin tetrachloride are used instead of titanium tetrachloride. 7.9 g (94% of theory) of solid crude product are obtained. The $^1$H-NMR spectrum shows that this product consists of about 60% of the starting ketone, 37% of R*, S*-carbinol and 3% of R*, R*-carbinol.

We claim:

1. A process for the preparation of a sterically pure β-triazolylcarbinol

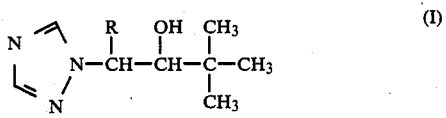

where R is
(a) phenoxy which is unsubstituted or contains up to three substituents of halogen, $CF_3$, methyl, methoxy, phenyl or phenoxy, or $C_1$-$C_{10}$-alkyl which is unsubstituted or monosubstituted or di- or trisubstituted by identical or different radicals from the group consisting of $C_1$-$C_4$-alkyl, methoxy, ethoxy, phenyl and phenoxy, which in turn can be substituted by halogen, $CF_3$, alkyl or alkoxy, by diastereoselective reduction of the corresponding α-triazolylketone (II) with a complex hydride which reduces ketones to alcohols, wherein the reaction is carried out in the presence of a Lewis acid in a non-polar solvent.

2. A process as claimed in claim 1, wherein the complex hydride used is a tetraalkylammonium borohydride, or a metal hydride which is soluble in aprotic solvents.

3. A process as claimed in claim 1, wherein the Lewis acid used is titanium tetrachloride, zinc chloride or tin tetrachloride.

4. A process as claimed in claim 1, wherein the product obtained consists predominantly of the R*, S*-diastereomer.

* * * * *